United States Patent
Crow et al.

(10) Patent No.: US 10,161,848 B2
(45) Date of Patent: Dec. 25, 2018

(54) METHODS FOR ALIGNING A LIGHT SOURCE WITH A FLOW STREAM AND SYSTEMS THEREOF

(71) Applicant: Becton, Dickinson and Company, Franklin Lakes, NJ (US)

(72) Inventors: Matthew J. Crow, Shoreline, WA (US); Valdis J. Riekstins, Woodinville, WA (US); Timothy Wayne Petersen, Seattle, WA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 0 days.

(21) Appl. No.: 14/947,984

(22) Filed: Nov. 20, 2015

(65) Prior Publication Data

US 2016/0169787 A1    Jun. 16, 2016

Related U.S. Application Data

(60) Provisional application No. 62/091,421, filed on Dec. 12, 2014.

(51) Int. Cl.
*G01N 15/14* (2006.01)
*G01N 15/10* (2006.01)

(52) U.S. Cl.
CPC ....... *G01N 15/1434* (2013.01); *G01N 15/147* (2013.01); *G01N 15/1459* (2013.01); *G01N 2015/1006* (2013.01); *G01N 2015/149* (2013.01); *G01N 2015/1452* (2013.01)

(58) Field of Classification Search
CPC ........... G01N 15/1434; G01N 15/1459; G01N 15/147; G01N 2015/1006; G01N 2015/149; G01N 15/1404
See application file for complete search history.

(56) References Cited

U.S. PATENT DOCUMENTS

| | | | |
|---|---|---|---|
| 4,487,320 A | 12/1984 | Auer | |
| 4,691,829 A | 9/1987 | Auer | |
| 5,101,113 A | 3/1992 | Hirleman, Jr. et al. | |
| 6,819,411 B1 | 11/2004 | Sharpe et al. | |
| 7,679,039 B2 | 3/2010 | Van Den Engh et al. | |
| 2003/0058445 A1* | 3/2003 | Fritz | G01B 11/272 356/399 |

(Continued)

FOREIGN PATENT DOCUMENTS

WO    2014151049 A1    9/2014

OTHER PUBLICATIONS

Lansdorp et al. "Optical monitor for measuring the amplitude and phase of perturbations on the surface of a capillary jet in a high-speed cell sorter", Rev. Sci. Instrum., vol. 75, No. 3, Mar. 2004, pp. 741-746.

*Primary Examiner* — Violeta A Prieto
(74) *Attorney, Agent, or Firm* — Khin K. Chin; Bret E. Field; Bozicevic, Field & Francis LLP

(57) ABSTRACT

Aspects of the present disclosure include methods and systems for assessing alignment of a light source with a flow stream. Methods according to certain embodiments include detecting first and second light signals along a vertical axis of the a light irradiated flow stream and calculating a differential signal amplitude between the first light signal and second light signal to assess the alignment of the light source with the flow stream. Systems for practicing the subject methods are also described.

23 Claims, 2 Drawing Sheets

(56) References Cited

U.S. PATENT DOCUMENTS

| | | | |
|---|---|---|---|
| 2005/0078299 A1 | 4/2005 | Fritz et al. | |
| 2005/0134850 A1* | 6/2005 | Rezachek | G01B 11/272 356/399 |
| 2008/0024758 A1 | 1/2008 | Tabata | |
| 2008/0259342 A1* | 10/2008 | van den Engh | G01N 15/1404 356/445 |
| 2010/0273208 A1 | 10/2010 | Tanenaka et al. | |
| 2014/0320861 A1* | 10/2014 | van den Engh | G01N 21/85 356/440 |
| 2016/0170168 A1* | 6/2016 | Rohani | G02B 7/022 356/338 |

* cited by examiner

METHODS FOR ALIGNING A LIGHT SOURCE WITH A FLOW STREAM AND SYSTEMS THEREOF

CROSS-REFERENCE TO RELATED APPLICATIONS

This application claims priority to U.S. Provisional Patent Application Ser. No. 62/091,421 filed Dec. 12, 2014, the disclosure of which application is incorporated herein by reference.

INTRODUCTION

Flow cytometry is a technique used to characterize and/or sort biological material, such as cells of a blood sample or particles of interest in any other type of biological or chemical sample. The technique may be used to record distributions and/or sort the biological material. A flow cytometer typically includes a sample reservoir for receiving a fluid sample, such as a blood sample, and a sheath reservoir containing a sheath fluid. The flow cytometer transports the particles (including cells) in the fluid sample as a cell stream to a flow cell, while also directing the sheath fluid to the flow cell. Within the flow cell, a liquid sheath is formed around the cell stream to impart a substantially uniform velocity on the cell stream. The flow cell hydrodynamically focuses the cells within the stream to pass through the center of a laser beam in a flow cell.

In flow cytometry, the flow stream is irradiated with a light source. The point at which the components of the flow stream intersect the light is generally referred to as the interrogation point. As components of the flow stream move through the interrogation point, it causes the light to scatter. Variations in the materials, such as morphologies or fluorescent label, may cause variations in the observed light and these variations allow for characterization and separation. To quantify these variations, the light must be collected. It is desirable to interrogate as much of the flow stream and to collect as much of the light from the flow stream as possible in order to maximize the speed and sensitivity of the procedure.

SUMMARY

Aspects of the disclosure include methods for assessing alignment of a light source (e.g., laser) with a flow stream, such as in a flow cytometer. Methods according to certain embodiments include detecting first and second light signals along a vertical axis of an irradiated flow stream, where the first and second light signals are obtained at different times, and calculating a differential signal amplitude between the first signal and second signals to assess the alignment of the light source with the flow stream.

In certain embodiments, methods include irradiating perturbations in the flow stream and detecting a first light signal and a second light signal. For instance, the perturbations in the flow stream may be produced by cells, non-cellular particles or beads in the flow stream. The first and second light signals may be forward propagated (e.g., scattered) light or as scattered light detected by total internal reflectance. In practicing methods according to some embodiments, assessing alignment of the light source (e.g., laser) with the flow stream includes determining a maximal differential signal amplitude between the first signal and the second signal. In some embodiments, methods further include adjusting the position of the laser to the position in the X-Y plane that produces the maximal differential signal amplitude or maintaining the position of the laser at the position that produces the maximal differential signal amplitude. In certain instances, the position of laser irradiation on the flow stream in an X-Y plane that produces the maximal differential signal amplitude is determined.

In embodiments, the first and second light signals are detected along a vertical axis of the flow stream. In some instances, the first and second light signals are detected at periodic intervals. In other instances, methods include continuously collecting the first and second light signals. The light signals are detected, in some instances, with a position sensing detector, such as a quadrant photodiode or a photodiode array have two or more photodiodes, such as three or more photodiodes.

Aspects of the present disclosure also include systems for practicing the subject methods. Systems according to certain embodiments include a light source, such as a laser (e.g., helium-neon laser), a sensor configured to detect first and second light signals along a vertical axis of the flow stream and a processor having memory operably coupled to the processor where the memory includes instructions to calculate a differential signal amplitude between the first and second light signals to assess the alignment of the laser with the flow stream.

In certain embodiments, the subject systems are configured to reduce the need for user input or manual alignment of a light source, flow stream or detector during or between sample analysis with a flow cytometer. In some embodiments, systems of interest may be partially or fully automated so that adjustments to the alignment of the light source and flow stream are processor controlled. In certain embodiments, the subject systems are configured to align the light source with the flow stream without any human input.

In some embodiments, the processor includes memory having instructions for determining a maximal differential signal amplitude between the first signal and the second signal. In these embodiments, the memory coupled to the processor may further include instructions for adjusting the position of the light source to irradiate the flow stream at the position that produces the maximal differential signal amplitude between the first signal and the second signal. In certain instances, the processor memory includes instructions for determining the position of irradiation on the flow stream in an X-Y plane that produces the maximal differential signal amplitude.

In some embodiments, the light source is a laser. In some instances, the laser is a continuous wave laser. In certain instances, the laser is a helium-neon laser. One or more lasers may be employed in the subject systems, such as 2 or more lasers and including 5 or more lasers. In certain embodiments, the laser is coupled to a support stage that is configured to adjust the position of the laser in in an X-Y plane. For example, the support stage may be configured to adjust the position of the laser in response to the calculated differential signal amplitude between a first light signal and a second light signal.

In some embodiments, sensors of the subject systems are configured to detect forward propagated (e.g., scattered) light from the flow stream. In other embodiments, the sensors are positioned to detect light propagated upstream by total internal reflectance. In these embodiments, the subject systems may further include a flow cell nozzle configured to propagate light upstream through the flow stream by total internal reflectance. For instance, the flow cell nozzle may include a nozzle chamber having a proximal end and a distal end, a nozzle orifice positioned at the distal end of the nozzle chamber such that the nozzle chamber is configured to direct propagated light from the flow stream to the proximal end of the nozzle chamber. Sensors of interest may include position sensing detectors, such as a quadrant photodiode or a photodiode array.

A system according to certain embodiments is provided for automatically aligning a laser (e.g., on a moveable support stage) with a flow stream by: determining a position of irradiation along the vertical axis of the flow stream that produces the maximal differential signal amplitude between a first light signal and a second light signal; and adjusting the position of the light source so that the position of light irradiation matches the position of irradiation on the flow stream that produces the maximal differential signal amplitude between the first signal and the second signal.

Aspects of the present disclosure also include computer controlled systems for practicing the subject methods, where the systems further include one or more computers having processors configured to automate one or more steps of the methods described herein. In some embodiments, systems include a computer having a computer readable storage medium with a computer program stored thereon, where the computer program when loaded on the computer includes algorithm for detecting first and second light signals along a vertical axis of a laser irradiated flow stream, wherein the first and second light signals are obtained at different times; algorithm for calculating a differential signal amplitude between the first signal and second signal and algorithm for assessing alignment of the laser with the flow stream based on the calculated differential signal amplitude between the first signal and second signal.

In certain embodiments, the subject computer controlled systems include one or more processors that are configured to adjust a position of light irradiation on a flow stream, where the processors include memory having instructions stored thereon that include algorithm for determining a position of irradiation on the flow stream that produces the maximal differential signal amplitude between the first signal and the second signal; algorithm for determining a current position of light irradiation on the flow stream in an X-Y plane; and algorithm for adjusting the position of light irradiation to match the position of irradiation on the flow stream that produces the maximal differential signal amplitude between the first signal and the second signal.

BRIEF DESCRIPTION OF THE FIGURES

The invention may be best understood from the following detailed description when read in conjunction with the accompanying drawings. Included in the drawings are the following figures.

DETAILED DESCRIPTION

Figure 1:
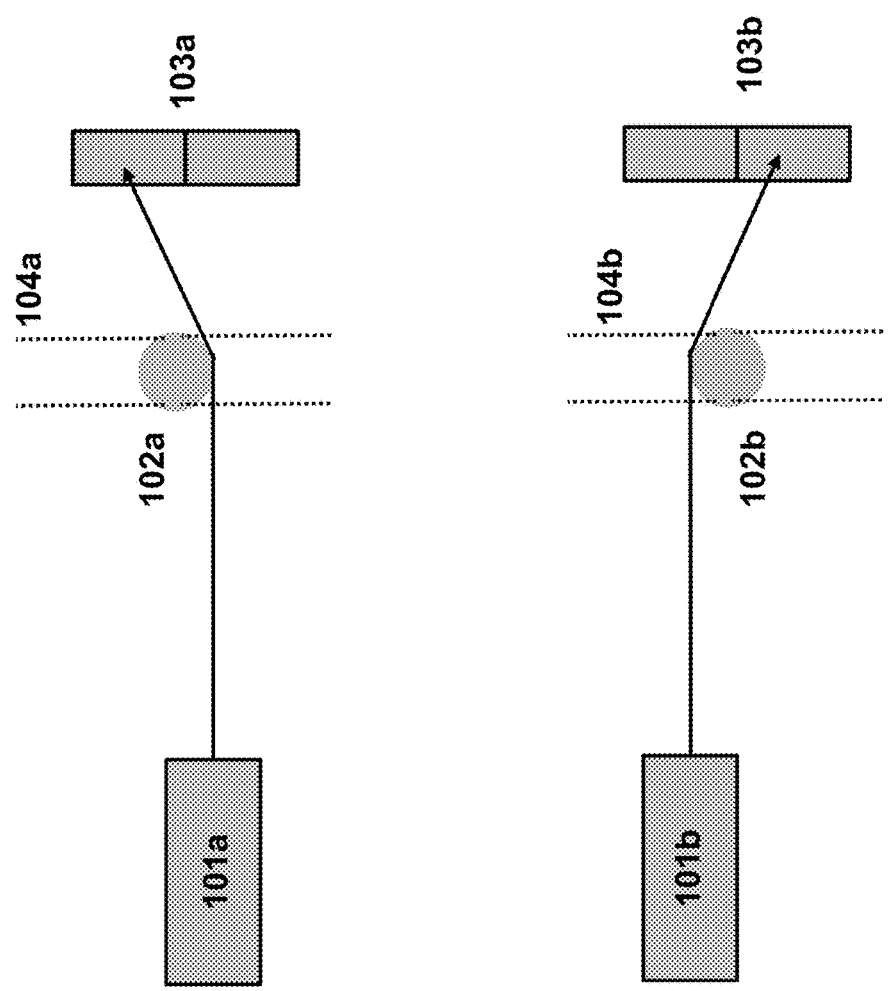
FIG. 1 depicts a side-view illustration assessing alignment of a light source with a flow stream according to certain embodiments.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the present disclosure provides methods for assessing alignment of a light source with a flow stream. In further describing embodiments of the disclosure, methods for assessing alignment of a light source (e.g., laser) with a flow stream are first described in greater detail. Next, systems suitable for practicing the subject methods to assess alignment of the light source with the flow stream are described. Computer controlled systems and kits are also provided.

Methods for Assessing Alignment of a Light Source with a Flow Stream

As summarized above, aspects of the disclosure include methods for assessing alignment of a light source (e.g., a laser) with a flow stream. In some embodiments, the subject methods include assessing alignment of a laser with a flow stream in a flow cytometer. Methods according to certain embodiments include detecting first and second light signals along a vertical axis of an irradiated flow stream, where the first and second light signals are obtained at different times, and calculating a differential signal amplitude between the first signal and second signal to assess the alignment of the light source with the flow stream. The phrase "assessing alignment" is used herein in its conventional sense to refer to determining the relative position of irradiation on the flow stream by the light source. In some embodiments, assessing alignment of the light source with the flow stream includes determining the position of irradiation by the light source along the horizontal axis of the flow stream. As described herein, the horizontal axis of the flow stream refers to an axis orthogonal to the direction of fluidic flow (i.e., longitudinal axis) of the flow stream. In other embodiments, assessing alignment of the light source with the flow stream includes determining whether the position of irradiation by the light source is displaced from the center (i.e., off-center) of the flow stream. For example, methods may include determining that the position of irradiation by the light source is displaced from the center of the flow stream by 1 μm or more along the horizontal axis of the flow stream, such as 2 μm or more, such as 3 μm or more, such as 5 μm or more, such as 10 μm or more, such as 25 μm or more, such 50 μm or more, such as 75 μm or more and including by 100 μm or more from the center of the flow stream along the horizontal axis. Depending on the spatial width of irradiation (e.g., laser beam width) by the light source, methods may include determining that the position of irradiation by the light source is displaced from the center of the flow stream by 0.01% or more of the irradiation width of the light source, such as by 0.05% or more, such as by 0.1% or more, such as by 0.5% or more, such as by 1% or more, such as by 2% or more, such as by 3% or more, such as by 5% or more, such as by 10% or more, such as by 25% or more and including by 50% or more of the irradiation width of the light source. In certain embodiments, assessing alignment of the light source with the flow stream includes determining whether the position of irradiation by the light source is at the center of the flow stream.

As described in greater detail below, in certain embodiments light irradiated onto a flow stream is refracted by perturbations in the flow stream. (FIG. 1) Perturbations in the flow stream may include components of a sample in the flow stream, such as cells, beads, non-cellular particles, large biological macromolecules, etc. In some instances, perturbation 102a in flow stream 104a refracts light from light source 101a in an upward direction to detector 103a at a first time period (FIG. 1, top). At a second time period light from light source 101b is refracted by perturbation 102b in flow stream 104b in a downward direction to detector 103b (FIG. 1, bottom). Accordingly, light signals collected during the first time period are signals from light refracted by the perturbation in an upward direction and light signals collected during the second time period are signals from light refracted by the perturbation in a downward direction. In some embodiments, a perturbation flowing in the flow stream refracts light in an upward direction (relative to the line of irradiation by the light source) as the perturbation crosses into the beam of irradiation. After passing through the beam of irradiation the perturbation refracts light in a downward direction as the perturbation flowing in the flow stream crosses out of the beam of irradiation. In these embodiments, the difference between the amplitude of the light signal from the upward refracted light and the downward refracted light may be calculated giving a differential signal amplitude. In some instances, a maximal differential signal amplitude (i.e., the highest difference in signal amplitude between upward refracted light and downward refracted light) is obtained where the spatial width of irradiation is centered with the center of the flow stream. (FIG. 2) In other words, in these embodiments the highest differential signal amplitude is obtained where the center of the spatial width of irradiation is aligned with the center of the flow stream along the horizontal axis. In other instances, a low differential signal amplitude is obtained where the spatial width of irradiation is off-center from the center of the flow stream, such as where the spatial width of irradiation by the light source is centered with an edge of the flow stream. In some embodiments of the present disclosure, the differential signal amplitude increases as the center of the spatial width of irradiation is displaced from an edge of the flow stream to the center of the flow stream.

In practicing methods according to certain embodiments, one or more signals from an irradiated flow stream (e.g., laser-irradiated flow stream) are detected along a vertical axis. In embodiments, the flow stream is irradiated with a light source, such as a laser and light scattered by the flow stream is collected and detected. The flow stream may be irradiated at any suitable vertical position along the flow stream so long as light signals from scattered light by the flow stream are sufficiently detected. In certain embodiments, the flow stream is a flow cytometer flow stream and the light source is a laser configured to irradiate the flow stream at a position immediately adjacent to the flow cell nozzle orifice. In other embodiments, the flow stream is irradiated at a position downstream from the flow cell nozzle orifice, such as at a position 0.001 mm from the flow cell nozzle orifice, such as 0.005 mm or more, such as 0.01 mm or more, such as 0.05 mm or more, such as 0.1 mm or more, such as 0.5 mm or more, such as 1 mm or more, such as 2 mm or more, such as 5 mm or more and including 10 mm or more downstream from the flow cell nozzle orifice. The flow stream may be irradiated at one or more vertical positions, such as at 2 or more, such as at 3 or more, such as at 4 or more, such as at 5 or more and including irradiating the flow stream at 10 or more vertical positions.

In embodiments, the flow stream may be irradiated with any suitable broadband or narrow band source of light. Depending on the components in the flow stream (e.g., cells, beads, non-cellular particles, etc.), the wavelength of light used to assess alignment of the light source with the flow stream may vary, ranging from 200 nm to 1500 nm, such as from 250 nm to 1250 nm, such as from 300 nm to 1000 nm, such as from 350 nm to 900 nm and including from 400 nm to 800 nm. For example, the light source may include a broadband light source emitting light having wavelengths from 200 nm to 900 nm. In other instances, the light source includes a narrow band light source emitting a wavelength ranging from 200 nm to 900 nm. For example, the light source may be a narrow band LED (1 nm-25 nm) emitting light having a wavelength ranging between 200 nm to 900 nm. In some embodiments, the light source is a laser, such as continuous wave laser. For example, the laser may be a diode laser, such as an ultraviolet diode laser, a visible diode laser and a near-infrared diode laser. In some instances, the diode laser outputs light at wavelengths ranging from 375 nm to 1000 nm, such as from 405 nm to 875 nm, such as from 450 nm to 800 nm, such as from 500 nm to 650 nm and including from 525 nm to 625 nm. In certain embodiments, lasers of interest include a 405 nm diode laser. In other embodiments, lasers of interest include a 488 nm diode laser. In yet other embodiments, the laser may be a helium-neon (HeNe) laser. In certain embodiments, the light source is a laser in a flow cytometer and methods include assessing alignment of the laser with a flow stream in a flow cytometer.

In other embodiments, the light source is a non-laser light source, such as a lamp, including but not limited to a halogen lamp, deuterium arc lamp, xenon arc lamp, a light-emitting diode, such as a broadband LED with continuous spectrum, superluminescent emitting diode, semiconductor light emitting diode, wide spectrum LED white light source, an multi-LED integrated. In some instances the non-laser light source is a stabilized fiber-coupled broadband light source, white light source, among other light sources or any combination thereof.

Depending on the spatial width of irradiation on the flow stream by the light source desired, the flow stream may be irradiated with the light source through one or more optical adjustment protocols. By "optical adjustment" is meant that a parameter of irradiation by the light source may be changed as desired, such as to increase or decrease the width of irradiation on the flow stream, the position of irradiation on the flow stream, the irradiation direction, wavelength of light output from the lights source, beam profile, beam width, beam intensity, focal point of the light source, pulse width or some other parameter. In some instances, optical adjustment is a magnification protocol configured to increase the width of irradiation on the flow stream by the light source, such as by 1% or greater, such as by 5% or greater, such as by 10% or greater, such as by 25% or greater, such as by 50% or greater and including increasing width of irradiation on the flow stream by 75% or greater. In other instances, optical adjustment is a de-magnification protocol configured to decrease the width of irradiation on the flow stream by the light source, such as by 1% or greater, such as by 5% or greater, such as by 10% or greater, such as by 25% or greater, such as by 50% or greater and including decreasing the width of irradiation on the flow stream by the light source by 75% or greater. In still other instances, the optical adjustment protocol is a collimating protocol.

The spatial cross-section of irradiation by the light source may be adjusted with any convenient optical adjustment protocol, including but not limited to lenses, mirrors, filters, fiber optics, wavelength separators, pinholes, slits, collimating protocols and combinations thereof. In certain embodiments, the spatial width of irradiation by the light source on the flow stream is optically adjusted with a focusing lens. The focusing lens, in one example may be a de-magnifying lens. In another example, the focusing lens is a magnifying lens. In other embodiments, the spatial width of irradiation by the light source on the flow stream is adjusted with one or more mirrors. In still other embodiments, the spatial width of irradiation by light source is adjusted with fiber optics.

The flow stream may be irradiated by the light source at any suitable distance from the flow stream, such as at a distance of 0.001 mm or more from the flow stream, such as 0.005 mm or more, such as 0.01 mm or more, such as 0.05 mm or more, such as 0.1 mm or more, such as 0.5 mm or more, such as 1 mm or more, such as 5 mm or more, such as 10 mm or more, such as 25 mm or more and including at a distance of 100 mm or more from the flow stream. Likewise, the flow stream may be irradiated by the light source at any suitable angle with respect to the vertical axis of the flow stream (i.e., the angle the beam of irradiation makes with the vertical axis of the flow stream), such as at an angle ranging from 10° to 90°, such as from 15° to 85°, such as from 20° to 80°, such as from 25° to 75° and including from 30° to 60°. In certain embodiments, the flow stream is irradiated by the light source at a 90° angle with respect to the vertical axis of the flow stream (i.e., irradiation by the light source is orthogonal to the vertical axis of the flow stream)

In assessing alignment of the light source with flow stream, the flow stream may be irradiated continuously or in discrete intervals. In some instances, methods include irradiating the flow stream with the light source continuously, such as where alignment of the light source with the flow stream is monitored by collecting real-time data. In other instances, methods include irradiating the flow stream with the light source in discrete intervals, such as irradiating the flow stream every 0.001 milliseconds, every 0.01 milliseconds, every 0.1 milliseconds, every 1 millisecond, every 10 milliseconds, every 100 milliseconds and including every 1000 milliseconds, or some other interval. Where the flow stream is irradiated at discrete intervals, the frequency of irradiation may depend such as on the concentration of components in the flow stream (e.g., cells, bead, non-cellular particles) as well as the flow rate of the flow stream.

In practicing embodiments of the subject methods, first and second light signals are detected along a vertical axis of the irradiated flow stream. The light signals may be detected at any suitable distance from the flow stream so long as a usable light signal is detected. For example, the light signals may detected at 0.01 mm or more from the flow stream, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more from the flow stream. The light signals may also be detected at any angle from the flow stream. For example, light signals may be detected at an angle with respect to the vertical axis of the flow stream which ranges from 10° to 90°, such as from 15° to 85°, such as from 20° to 80°, such as from 25° to 75° and including from 30° to 60°. In some instances, detectors (as described in greater detail below) are positioned at 30° to 60° with respect to the vertical axis of the flow stream.

One or more light signals may be detected at each position irradiated along the flow stream by the light source, as described above. For example, two or more light signals, such as three or more light signals, such as four or more light signals, such as five or more light signals and including 10 or more light signals may be detected at each position irradiated along the flow stream by the light source. Where irradiation is continuous, one or more light signals may be detected at different times while irradiating the flow stream, such as two or more light signals, such as three or more light signals, such as four or more light signals, such as five or more light signals and including 10 or more light signals may be detected at different times while irradiating the flow stream.

In certain embodiments, light signals from the irradiated flow stream are from light detected by one or more detectors positioned adjacent to the flow stream in a forward configuration from the light source. For example, the light signals from the irradiated flow stream may be detected by one or more detectors configured as forward scatter detectors. In other embodiments, light signals from the irradiated flow stream is light propagated upstream by total internal reflectance. The term "propagate" is used herein in its conventional sense to refer to the travel of light through the fluid medium of the flow stream where the path of propagated light is a function of the refraction, reflection, diffraction and interference by the fluid medium. In these embodiments, light refracted by the flow stream is propagated upstream by total internal reflectance. By "upstream" is meant that the emitted light is propagated and collected in a direction which is opposite to the direction of fluid flow by the flow stream. In other words, where the flow stream has fluidic flow along the positive Y direction along the Y axis in an X-Y plane, light signals from light propagated upstream by total internal reflectance traverses in the negative Y direction. The phrase "total internal reflectance" is used herein in its conventional sense to refer to the propagation of electromagnetic waves within the boundaries of a fluid medium (e.g., flow stream) such that when a propagating wave strikes the medium boundary at an angle larger than the critical angle with respect to the normal to the surface, the electromagnetic wave is internally reflected. In particular, where the refractive index is lower on the other side of the fluid medium boundary and the incident angle is greater than the critical angle, the propagating light wave does not pass through the boundary and is internally reflected.

In some embodiments, the subject methods include assessing alignment of a light source with a flow stream in a flow cytometer where light signals from the irradiated flow stream is propagated upstream by total internal reflectance. In certain instances, methods for detecting light signals from light propagated upstream by total internal reflectance include, but are not limited to those described in U.S. patent application Ser. No. 14/260,177 filed on Apr. 23, 2014, the disclosure of which is herein incorporated by reference.

In some embodiments, detecting first and second light signals from the irradiated flow stream includes moving the light source and one or more detectors alongside the path of the flow stream. For instances, the light source and detectors may be moved upstream or downstream alongside the flow stream detecting first and second light signals at a plurality of the positions along the vertical axis of the flow stream. In embodiments, a first and second light may be detected at one or more vertical positions along the flow stream, such as at 2 or more positions, such as at 3 or more positions, such as at 5 or more positions and including at 10 or more vertical positions along the flow stream. Where the light signals are collected at more than one vertical position along the flow stream, the distance between each position along the flow stream may vary, such as being separated by 0.001 mm or more, such as by 0.005 mm or more, such as by 0.01 mm or more, such as by 0.05 mm or more, such as by 0.1 mm or more, such as by 0.5 mm or more, such as by 1 mm or more, such as by 5 mm or more, such as by 10 mm or more, such as by 25 mm or more and including detecting light signals at two or more vertical positions that are separated by 100 mm or more.

The light signals may be detected by any convenient positional sensing detecting protocol, including but not limited to photosensors or photodetectors, such as active-pixel sensors (APSs), quadrant photodiodes, image sensors, charge-coupled devices (CODs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, the light signals are detected with a quadrant photodiode. Where the light signals are detected with a quadrant photodiode, the active detecting surface area of each region of the quadrant photodiode may vary, such as from $0.01$ $cm^2$ to $10$ $cm^2$, such as from $0.05$ $cm^2$ to $9$ $cm^2$, such as from, such as from $0.1$ $cm^2$ to $8$ $cm^2$, such as from $0.5$ $cm^2$ to $7$ $cm^2$ and including from $1$ $cm^2$ to $5$ $cm^2$. In some instances, the photodetector is a photodiode array having more than one photodiode, such as two or more photodiodes, such as three or more, such as five or more and including 10 or more photodiodes.

As summarized above, the difference in amplitude between the first light signal and the second light signal is calculated to determine a differential signal amplitude. The differential signal amplitude between the first and second light signals may be calculated in conjunction with detecting the first and second light signals or may be conducted after a predetermined duration following detection of the light signals. In some embodiments, the differential signal amplitude between the first and second light signals is continuously calculated in conjunction with detection of the light signals. In other embodiments, the differential signal amplitude between the first and second light signals is calculated at a predetermined duration after detection of the light signals, such as 0.001 seconds or longer after detection of the first and second light signals, such as 0.01 seconds or longer, such as 0.1 seconds or longer, such as 0.5 seconds or longer, such as 1 second or longer and including 5 seconds or longer after detection of the first and second light signals.

In practicing the subject methods, the alignment of the light source with the flow stream is assessed based on the calculated differential signal amplitude between the first and second light signals. In some embodiments, the light source and flow stream are determined to be aligned when the differential signal amplitude is at or above a predetermined threshold. In other embodiments, the light source and flow stream are determined to be not aligned when the differential signal amplitude is below a predetermined threshold.

In other embodiments, the calculated differential signal amplitude is compared with a maximal differential signal amplitude to assess alignment of the light source with the flow stream. The maximal differential signal amplitude may be a predetermined maximal differential signal amplitude or may be determined specifically for a particular flow stream and light source. In some instances, the maximal differential signal amplitude is predetermined based the parameters of the flow stream and light source, such as the diameter of the flow stream (e.g., as estimated by flow cell nozzle orifice in a flow cytometer), the spatial width of irradiation of the light source and type of photodetector (e.g., quadrant photodiode) employed.

In other instances, the subject methods include determining a maximal differential signal amplitude for a particular light source and flow stream. In some embodiments, determining a maximal differential signal amplitude includes detecting a plurality of sets of first and second light signals; calculating a differential signal amplitude for each set of first and second light signals and determining the maximal differential signal amplitude from the plurality of calculated differential signal amplitudes. In some instances, the plurality of first and second light signals are detected by adjusting the position of irradiation by the light source on the flow stream in discrete increments and measuring first and second light signals at each increment. For example, the light source may be displaced along the horizontal axis of the flow stream in discrete increments, such as in increments of 0.001 mm or more, such as 0.005 mm or more, such as 0.01 mm or more, such as 0.05 mm or more, such as 0.1 mm or more, such as 0.5 mm or more, such as 1 mm or more, such as 2 mm or more and including displacing the light source along the horizontal axis of the flow stream in increments of 5 mm or more.

In other embodiments, determining a maximal differential signal amplitude includes displacing the light source across the flow stream along the horizontal axis in a continuous manner; collecting first and second light signals at predetermined time intervals; calculating a differential signal amplitude from each of the collected first and second light signals and determining the maximal differential signal amplitude from the calculated differential signal amplitudes. In these embodiments, first and second light signals are collected at predetermined time intervals, such as every 0.001 milliseconds or more, such as every 0.005 milliseconds or more, such as every 0.01 milliseconds or more, such as every 0.05 milliseconds or more, such as every 0.1 milliseconds or more, such as every 0.5 milliseconds or more, such as every 1 millisecond or more, such as every 5 milliseconds or more, such as every 10 milliseconds or more, such as every 25 milliseconds or more and including every 100 milliseconds or more.

In assessing alignment of the light source and flow stream by comparing the calculated differential signal amplitude with a maximal differential signal amplitude, the light source in certain instances, is determined to be not aligned with the flow stream when the calculated differential signal amplitude is less than the maximal differential signal amplitude. In other instances, the light source is determined to be not aligned with the flow stream when the difference between the calculated differential signal amplitude and maximal differential signal amplitude exceeds a predetermined threshold. For example, the light source is determined to be not aligned with the flow stream when the calculated differential signal amplitude is less than the maximal differential signal amplitude by 1% or more, by 2% or more, by 5% or more, by 10% or more, by 15% or more, by 20% or more, by 25% or more and including by 50% or more.

In some embodiments, methods include determining a position of irradiation by the light source on the flow stream in along a horizontal axis orthogonal to the longitudinal axis of the flow stream that produces the maximal differential signal amplitude between the first light signal and the second light signal. For instance, methods may include capturing images of the irradiated flow stream and mapping the spatial position of the irradiation on the flow stream along the horizontal axis. For example, one or more images of the irradiated flow stream may be captured, such as 2 or more images, such as 3 or more images, such as 5 or more images and including 10 or more images of the irradiated flow stream may be captured. Based on the determined spatial position of irradiation by the light source on the flow stream, methods may include generating a data signal corresponding to the spatial position of irradiation by the light source on the flow stream that produces the maximal differential signal amplitude between the first signal and the second signal. In some embodiments, the position of irradiation by the light source on the flow stream that produces the maximal differential signal amplitude between the first signal and the second signal is where the spatial width of irradiation is centered with the center of the flow stream. In other embodiments, the position of irradiation by the light source on the flow stream that produces the maximal differential signal amplitude between the first signal and the second signal is where the spatial width of irradiation is displaced from the center of the flow stream by 0.001 µm or more along the horizontal axis of the flow stream, such as by 0.005 µm or more, such as by 0.01 µm or more, such as by 0.05 µm or more, such as by 0.1 µm or more, such as by 0.5 µm or more, such as by 1 µm or more, such as 2 µm or more, such as 3 µm or more, such as 5 µm or more, such 50 µm or more, such as 75 µm or more and including by 100 µm or more from the center of the flow stream along the horizontal axis.

In certain embodiments, the light source is adjusted in response to the assessed alignment of the light source with the flow stream. For example, in some instances where the position of irradiation on the flow stream by the light source is determined to produce a differential signal amplitude between the first signal and the second signal that is less than maximal, the light source may be displaced in along the horizontal axis to the position which produces a maximal differential signal amplitude between a first light signal and second light signal. In these instances, methods may include mapping the position of the light source along the horizontal axis that produces the maximal differential signal amplitude between a first light signal and second light signal and matching the position of the light source along the horizontal axis with the position which produces the maximal differential signal amplitude between a first light signal and second light signal.

In certain embodiments, methods include determining a position of irradiation by the light source on the flow stream in an X-Y plane that produces the maximal differential signal amplitude between the first light signal and the second light signal. For instance, methods may include capturing images of the irradiated flow stream and mapping the spatial position of the irradiation on the flow stream in an X-Y plane. For example, one or more images of the irradiated flow stream may be captured, such as 2 or more images, such as 3 or more images, such as 5 or more images and including 10 or more images of the irradiated flow stream may be captured. Based on the determined spatial position of irradiation by the light source on the flow stream, methods may include generating a data signal corresponding to the spatial position of irradiation by the light source on the flow stream that produces the maximal differential signal amplitude between the first signal and the second signal. In some embodiments, the position of irradiation by the light source on the flow stream that produces the maximal differential signal amplitude between the first signal and the second signal is where the spatial width of irradiation is centered with the center of the flow stream. In other embodiments, the position of irradiation by the light source on the flow stream that produces the maximal differential signal amplitude between the first signal and the second signal is where the spatial width of irradiation is displaced from the center of the flow stream by 0.001 µm or more along the horizontal axis of the flow stream, such as by 0.005 µm or more, such as by 0.01 µm or more, such as by 0.05 µm or more, such as by 0.1 µm or more, such as by 0.5 µm or more, such as by 1 µm or more, such as 2 µm or more, such as 3 µm or more, such as 5 µm or more, such as 10 µm or more, such as 25 µm or more, such 50 µm or more, such as 75 µm or more and including by 100 µm or more from the center of the flow stream along the horizontal axis.

In embodiments, the light source may be adjusted in response to the assessed alignment of the light source with the flow stream. For example, in some instances where the position of irradiation on the flow stream by the light source is determined to produce a differential signal amplitude between the first signal and the second signal that is less than maximal, the light source may be displaced in an X-Y plane to the position which produces a maximal differential signal amplitude between a first light signal and second light signal. In these instances, methods may include mapping the position of the light source in the X-Y plane that produces the maximal differential signal amplitude between a first light signal and second light signal and matching the position of the light source in the X-Y plane with the position which produces the maximal differential signal amplitude between a first light signal and second light signal.

The position of the irradiation by the light source on the flow stream may be adjusted by any convenient protocol, such as by directly moving the light source, moving a support stage coupled to the light source as well as changing the position, configuration or orientation of one or more optical adjustment protocols (as described above). In some embodiments, the position of irradiation by the light source on the flow stream is adjusted by changing the orientation (e.g., tilt) of a lens or mirror between the light source and the flow stream. For example, the orientation of the optical adjustment protocol (e.g., a mirror) may be changed to position the beam of light on a different part of the flow stream, such as by increasing the angle of the optical adjustment protocol by 5° or more, such as by 10° or more, such as by 15° or more, such as by 20° or more, such as by 30° or more, such as by 45° or more, such as by 60° or more and including by 75° or more. In certain embodiments, methods include adjusting the position of irradiation of light onto a different part of the flow stream by changing the angle of the mirror with respect to the flow stream by 5° or more, such as by 10° or more, such as by 15° or more, such as by 20° or more, such as by 30° or more, such as by 45° or more, such as by 60° or more and including by 75° or more.

In certain embodiments, methods include assessing alignment of a light source with a flow stream and automatically adjusting the light source so that irradiation by the light source on the flow stream is aligned. By "automatic" is meant that adjustments to the position of the light source made in response to the calculated differential signal amplitude or in response to a comparison between the calculated differential signal amplitude and maximal differential signal amplitude requires little to no human intervention or manual input. In certain embodiments, the position of irradiation by the light source on the flow stream is adjusted in accordance with the subject methods without any human intervention. For example, in certain embodiments, methods include automatically aligning a laser with a flow stream in a flow cytometer and without any input by the user of the flow cytometer by: detecting a first light signal and a second light signal from the laser irradiated flow stream; calculating a differential signal amplitude between the first light signal and the second light signal; comparing the calculated differential signal amplitude with a maximal differential signal amplitude; and matching the position of the laser irradiation on the flow stream with the position of the laser irradiation on the flow stream which produces the maximal differential signal amplitude between a first light signal and a second light signal from the laser irradiated flow stream.

In some embodiments, after matching the light source with the position which produces the maximal differential signal amplitude, the light source may be maintained in this position for a predetermined duration before reassessing alignment of the light source with the flow stream, such as for 1 minute or longer, such as 5 minutes or longer, such as 15 minutes or longer, such as 30 minutes or longer, such as 60 minutes or longer, such as for 6 hours or more, such as for 12 hours or more, such as for 24 hours or more, such as for 48 hours or more, such as for 72 hours or more and including maintaining the position of the light source for 168 hours or more before reassessing alignment of the light source with the flow stream, or for some other interval.

In some embodiments, methods of the present disclosure include reassessing the alignment of a light source with a flow stream. The alignment of the light source with the flow stream may be reassessed at any time as desired, such as after a predetermined duration or in response to an event where it may be desirable to evaluate alignment of a light source with the flow stream. For example, the alignment of the light source with the flow stream may be reassessed every 5 minutes, every 10 minutes, every 30 minutes, every 60 minutes, every 6 hours, every 12 hours, every 24 hours, every 48 hours, every 72 hours, every 168 hours or some other interval. In other embodiments, the alignment of the light source with flow stream may be reassessed after an event which might change the alignment of the light source with the flow stream. For example, alignment of the light source with flow stream may be reassessed after the light source is changed or modified, such as installing a new laser in a flow cytometer or where the flow stream is changed, such as changing a flow cell nozzle in a flow cytometer.

In other embodiments, the alignment of the light source with the flow stream may be assessed continuously. For example, the alignment of a laser with the flow stream in a flow cytometer may be continuously monitored by collecting real-time data.

Systems for Assessing Alignment of a Light Source with a Flow Stream

Aspects of the present disclosure also include systems for assessing alignment of a light source (e.g., laser) with a flow stream. In some embodiments, the subject systems include a laser and a flow stream of a flow cytometer. Systems according to certain embodiments include a light source, a sensor configured to detect first and second light signals along a vertical axis of the flow stream and a processor having memory operably coupled to the processor where the memory includes instructions to calculate a differential signal amplitude between the first and second light signals to assess the alignment of the light source with the flow stream. As described above, the term "assessing alignment" is used herein in its conventional sense to refer to determining the relative position of irradiation on the flow stream by the light source. In some embodiments, the subject systems are configured to assess alignment of the light source with the flow stream by determining the position of irradiation by the light source along the horizontal axis of the flow stream. In other embodiments, the subject systems are configured to assess alignment of the light source with the flow stream by determining whether the position of irradiation by the light source is displaced from the center (i.e., off-center) of the flow stream. For example, the subject systems may provide to the user that the position of irradiation by the light source is displaced from the center of the flow stream by 1 µm or more along the horizontal axis of the flow stream, such as 2 µm or more, such as 3 µm or more, such as 5 µm or more, such as 10 µm or more, such as 25 µm or more, such 50 µm or more, such as 75 µm or more and including by 100 µm or more from the center of the flow stream along the horizontal axis. In other embodiments, systems of interest may determine that the position of irradiation by the light source is displaced from the center of the flow stream by 0.01% or more of the irradiation width of the light source, such as by 0.05% or more, such as by 0.1% or more, such as by 0.5% or more, such as by 1% or more, such as by 2% or more, such as by 3% or more, such as by 5% or more, such as by 10% or more, such as by 25% or more and including by 50% or more of the irradiation width of the light source. In certain embodiments, the subject systems are configured assess whether the position of irradiation by the light source is at the center of the flow stream.

In certain embodiments, systems of interest may be fully automated so that assessing alignment between the light source and the flow stream is processor controlled. By "fully automated" is meant that assessing alignment between the light source and the flow stream requires little to no human intervention or manual input into the subject systems. In certain embodiments, the subject systems are configured to assess alignment of the light source with the flow stream without any human intervention.

As summarized above, systems of interest include a light source. In embodiments, the light source may be any suitable broadband or narrow band source of light. Depending on the components in the flow stream (e.g., cells, beads, non-cellular particles, etc.), the light source may be configured to emit wavelengths of light that vary, ranging from 200 nm to 1500 nm, such as from 250 nm to 1250 nm, such as from 300 nm to 1000 nm, such as from 350 nm to 900 nm and including from 400 nm to 800 nm. For example, the light source may include a broadband light source emitting light having wavelengths from 200 nm to 900 nm. In other instances, the light source includes a narrow band light source emitting a wavelength ranging from 200 nm to 900 nm. For example, the light source may be a narrow band LED (1 nm-25 nm) emitting light having a wavelength ranging between 200 nm to 900 nm. In some embodiments, the light source is a laser, such as continuous wave laser. For example, the laser may be a diode laser, such as a ultraviolet diode laser, a visible diode laser and a near-infrared diode laser. In some instances, the diode laser outputs light at wavelengths ranging from 375 nm to 1000 nm, such as from 405 nm to 875 nm, such as from 450 nm to 800 nm, such as from 500 nm to 650 nm and including from 525 nm to 625 nm. In certain embodiments, lasers of interest include a 405 nm diode laser. In other embodiments, the laser may be a helium-neon (HeNe) laser. In certain embodiments, the light source is a laser in a flow cytometer.

In other embodiments, the light source is a non-laser light source, such as a lamp, including but not limited to a halogen lamp, deuterium arc lamp, xenon arc lamp, a light-emitting diode, such as a broadband LED with continuous spectrum, superluminescent emitting diode, semiconductor light emitting diode, wide spectrum LED white light source, an multi-LED integrated. In some instances the non-laser light source is a stabilized fiber-coupled broadband light source, white light source, among other light sources or any combination thereof.

Depending on the spatial width of irradiation on the flow stream by the light source desired, systems of interest may also include one or more optical adjustment protocols coupled with the light source. As discussed above, the term "optical adjustment" refers to any device that is capable of changing the spatial width irradiation or some other characteristic of irradiation from the light source, such as for example, irradiation position on the flow stream, irradiation direction, wavelength, beam profile, beam width, beam intensity, focal point and pulse width. For example, systems may include an optical adjustment protocol that increases or decreases the spatial width of irradiation of the light source. In some instances, optical adjustment is a magnification protocol configured to increase the spatial width of irradiation by the light source, such as by 1% or greater, such as by 5% or greater, such as by 10% or greater, such as by 25% or greater, such as by 50% or greater and including a magnification protocol that increases width of irradiation by the light source by 75% or greater. In other instances, optical adjustment is a de-magnification protocol configured to decrease the spatial width of irradiation by the light source, such as by 1% or greater, such as by 5% or greater, such as by 10% or greater, such as by 25% or greater, such as by 50% or greater and including a de-magnification protocol that decreases the width of irradiation by the light source by 75% or greater. In still other instances, the optical adjustment protocol is a collimating protocol.

In embodiments, optical adjustment protocols may be any convenient device which adjusts one or more characteristics of the light source, including but not limited to lenses, mirrors, filters, fiber optics, wavelength separators, pinholes, slits, collimating protocols and combinations thereof. In certain embodiments, systems of interest include one or more focusing lenses. The focusing lens, in one example may be a de-magnifying lens. In another example, the focusing lens is a magnifying lens. In other embodiments, systems of interest include one or more mirrors. In still other embodiments, systems of interest include fiber optics.

In some embodiments, optical adjustment components are movable. For instance, in one example a mirror may be moved to adjust laser alignment with the flow stream. In some instances, the optical adjustment component is movable in two dimensions, such as in an X-Y plane orthogonal to the axis of the flow stream. In other instances, the optical adjustment component is movable in three dimensions. In certain embodiments, the optical adjustment component is a mirror configured to be moved to adjust the position of irradiation on the flow stream by the light source. In some embodiments, the mirror may be configured to be moved in an X-Y plane such as along the axis of the flow stream. In other embodiments, the mirror is configured to change angles, such as tilted with respect the light stream or the flow stream. For example, systems may be configured to change the position of irradiation of light onto a different part of the flow stream by changing the angle of the mirror with respect to the flow stream by 5° or more, such as by 10° or more, such as by 15° or more, such as by 20° or more, such as by 30° or more, such as by 45° or more, such as by 60° or more and including by 75° or more.

Where the optical adjustment component (e.g., mirror) is configured to move, the optical adjustment component may be configured to be moved continuously or in discrete intervals. In some embodiments, movement of the optical adjustment component is continuous. In other embodiments, the optical adjustment component is movable in discrete intervals, such as for example in 0.01 micron or greater increments, such as 0.05 micron or greater, such as 0.1 micron or greater, such as 0.5 micron or greater, such as 1 micron or greater, such as 10 micron or greater, such as 100 microns or greater, such as 500 microns or greater, such as 1 mm or greater, such as 5 mm or greater, such as 10 mm or greater and including 25 mm or greater increments.

Any displacement protocol may be employed to move optical adjustment component structures, such as coupled to a movable support stage or directly with a motor actuated translation stage, leadscrew translation assembly, geared translation device, such as those employing a stepper motor, servo motor, brushless electric motor, brushed DC motor, micro-step drive motor, high resolution stepper motor, among other types of motors.

The light source may be positioned at any suitable distance from the flow stream, such as at a distance of 0.001 mm or more from the flow stream, such as 0.005 mm or more, such as 0.01 mm or more, such as 0.05 mm or more, such as 0.1 mm or more, such as 0.5 mm or more, such as 1 mm or more, such as 5 mm or more, such as 10 mm or more, such as 25 mm or more and including at a distance of 100 mm or more from the flow stream. In addition, the light source may be positioned at any suitable angle to the vertical axis of the flow stream (i.e., the angle the beam of irradiation makes with the vertical axis of the flow stream), such as at an angle ranging from 10° to 90°, such as from 15° to 85°, such as from 20° to 80°, such as from 25° to 75° and including from 30° to 60°. In certain embodiments, the light source is positioned at a 90° angle with respect to the vertical axis of the flow stream (i.e., the light source is orthogonal to the vertical axis of the flow stream)

The light source may be configured to irradiate the flow stream continuously or in discrete intervals. In some instances, systems include a light source that is configured to irradiate the flow stream continuously, such as with a continuous wave laser that continuously irradiates the flow stream at the interrogation point in a flow cytometer. In other instances, systems of interest include a light source that is configured to irradiate the flow stream at discrete intervals, such as every 0.001 milliseconds, every 0.01 milliseconds, every 0.1 milliseconds, every 1 millisecond, every 10 milliseconds, every 100 milliseconds and including every 1000 milliseconds, or some other interval. Where the light source is configured to irradiate the flow stream at discrete intervals, systems may include one or more additional components to provide for intermittent irradiation of the flow stream with the light source. For example, the subject systems in these embodiments may include one or more laser beam choppers, manually or computer controlled beam stops for blocking and exposing the flow stream to the light source.

In certain embodiments, systems include one or more support stages coupled to the light source for adjusting the position of the light source, such as for example to align the light source with the flow stream. Suitable support stages may be any convenient mounting device configured to hold in place the light source and may include a planar substrate, contoured mounting devices, cylindrical or tubular support structures, laser or LED holders, among other types of support structures. In some instances, the support stage is a mount for a laser. Depending on the number of light sources in the subject systems, the number of support stages may vary, as desired, such as two or more, such as three or more, such as four or more and including five or more support stages. In certain embodiments, systems of interest include one support stage, such as a support stage having a mounted laser.

In some embodiments, support stages are movable. For instance, in one example the support stage may be moved to adjust the laser alignment with the flow stream. In some instances, the support stage is movable in two dimensions, such as in an X-Y plane orthogonal to the axis of the flow stream. In other instances, the support structure is movable in three dimensions. Where the support stage is configured to move, the support stage may be configured to be moved continuously or in discrete intervals. In some embodiments, the support stage is movable by continuous motion. In other embodiments, the support stage is movable in discrete intervals, such as for example in 0.01 micron or greater increments, such as 0.05 micron or greater, such as 0.1 micron or greater, such as 0.5 micron or greater, such as 1 micron or greater, such as 10 micron or greater, such as 100 microns or greater, such as 500 microns or greater, such as 1 mm or greater, such as 5 mm or greater, such as 10 mm or greater and including 25 mm or greater increments.

Any displacement protocol may be employed to move the support structures, such as moving the support stages with a motor actuated translation stage, leadscrew translation assembly, geared translation device, such as those employing a stepper motor, servo motor, brushless electric motor, brushed DC motor, micro-step drive motor, high resolution stepper motor, among other types of motors.

As discussed above, in assessing alignment of the light source with the flow stream, first and second light signals are detected along a vertical axis of the irradiated flow stream. In embodiments, the subject systems include one or more photodetectors for detecting light signals from the flow stream. Photodetectors in the subject systems may be any convenient positional sensing detecting protocol, including but not limited to photosensors or photodetectors, such as active-pixel sensors (APSs), quadrant photodiodes, image sensors, charge-coupled devices (CODs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, the systems of interest include a quadrant photodiode. For example the photodetector may be a quadrant photodiode having an active detecting surface area of each region that ranges from 0.01 cm$^2$ to 10 cm$^2$, such as from 0.05 cm$^2$ to 9 cm$^2$, such as from, such as from 0.1 cm$^2$ to 8 cm$^2$, such as from 0.5 cm$^2$ to 7 cm$^2$ and including from 1 cm$^2$ to 5 cm$^2$. In some instances, the photodetector is a photodiode array having more than one photodiode, such as two or more photodiodes, such as three or more, such as five or more and including 10 or more photodiodes.

The photodetector may be positioned at any suitable distance from the flow stream so long as a usable light signal is detectable. For example, detectors in the subject systems may be positioned 1 mm or more from the flow stream, such as 5 mm or more, such as 10 mm or more, such as 15 mm or more, such as 25 mm or more, such as 50 mm or more, such as 100 mm or more, such as 150 mm or more, such as 250 mm or more and including 500 mm or more from the flow stream. The detectors may also be positioned at any angle from the flow stream. For example, the detectors may be angled with respect to the vertical axis of the flow stream at from 10° to 90°, such as from 15° to 85°, such as from 20° to 80°, such as from 25° to 75° and including from 30° to 60°. In some instances, the one or more detectors are positioned at 30° to 60° with respect to the vertical axis of the flow stream.

In certain embodiments, the subject systems are configured to assess alignment of the light source with the flow stream by forward propagated (e.g., scattered) light from the irradiated flow stream and include one or more positioned adjacent to the flow stream in a forward configuration from the light source. For example, the light signals from the irradiated flow stream may be detected by one or more detectors configured as forward scatter detectors. In these embodiments, the forward scatter detectors are positioned on the opposite side of the flow stream from the light source and are positioned to collect and detect forward propagated (e.g., scattered) light. In other embodiments, the subject systems are configured to assess alignment of the light source with the flow stream by detecting light signals from light propagated upstream by total internal reflectance. As discussed above, light refracted by the flow stream is propagated upstream by total internal reflectance. In these embodiments, light is propagated and collected in a direction which is opposite to the direction of fluid flow by the flow stream. In other words, where the flow stream has fluidic flow along the positive Y direction along the Y axis in an X-Y plane, light signals from light propagated upstream by total internal reflectance traverses in the negative Y direction. In certain embodiments, flow cell nozzles and systems of interest for detecting light signals from light propagated upstream by total internal reflectance in a flow cytometer include, but are not limited to those described in U.S. patent application Ser. No. 14/260,177 filed on Apr. 23, 2014, the disclosure of which is herein incorporated by reference.

As summarized above, systems include one or more processor having memory operably coupled to the processor where the memory includes instructions to calculate a differential signal amplitude between a first light signal and a second light signal to assess alignment of a light source (e.g., laser) with a flow stream. In embodiments, the processor is configured to execute instructions from memory for assessing alignment of the light source with the flow stream and in some instances, adjust the position of the light source to match a position which produces the maximal differential signal amplitude between the first light signal and the second light signal from the irradiated flow stream. The processors include memory having a plurality of instructions for performing the steps of the subject methods (as described above), such as detecting first and second light signals at different times along a vertical axis of the irradiated flow stream, calculating a differential signal amplitude between the first signal and second signal and assessing alignment of the light source with the flow stream based on the calculated differential signal amplitude between the first light signal and second light signal. The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

In embodiments, the processor is configured to the difference in amplitude between the first light signal and the second light signal to determine a differential signal amplitude. In some embodiments, the processor calculates the differential signal amplitude between the first and second light signals in conjunction with detecting the first and second light signals. In other embodiments, the processor calculates the differential signal amplitude at a predetermined duration following detection of the light signals, such as 0.001 seconds or longer after detection of the first and second light signals, such as 0.01 seconds or longer, such as 0.1 seconds or longer, such as 0.5 seconds or longer, such as 1 second or longer and including 5 seconds or longer after detection of the first and second light signals.

In some embodiments, the processor includes memory having instructions to assess alignment of the light source with the flow stream based on the calculated differential signal amplitude between the first and second light signals. In some embodiments, the processor memory includes algorithm for determining that the light source and flow stream are aligned with the calculated differential signal amplitude is at or above a predetermined threshold. In other embodiments, the processor memory includes algorithm for determining that the light source and flow stream are not aligned when the calculated differential signal amplitude is below a predetermined threshold.

In certain embodiments, the processor memory includes algorithm for assessing alignment of the light source with the flow stream by comparing the calculated differential signal amplitude with a maximal differential signal amplitude. In assessing alignment of the light source and flow stream by comparing the calculated differential signal amplitude with a maximal differential signal amplitude, systems of interest may be configured to output to the user that the light source is not aligned with the flow stream when the calculated differential signal amplitude is less than the maximal differential signal amplitude. In other instances, systems may be configured to output to the user that the light source is not aligned with the flow stream when the difference between the calculated differential signal amplitude and maximal differential signal amplitude exceeds a predetermined threshold. For example, the system may alert the user that the light source and the flow stream are not aligned when the calculated differential signal amplitude is less than the maximal differential signal amplitude by 1% or more, by 2% or more, by 5% or more, by 10% or more, by 15% or more, by 20% or more, by 25% or more and including by 50% or more. Output from the processor may be communicated to the user by any convenient protocol, such as for example by displaying on a monitor or by printing a report.

As discussed above, in some instances the maximal differential signal amplitude is a predetermined maximal differential signal amplitude preloaded into the processor memory of the subject systems and is based on parameters of the flow stream and light source. For example, the preloaded maximal differential signal amplitude may be based on parameters such as diameter of the flow stream (e.g., as estimated by flow cell nozzle orifice in a flow cytometer), spatial width of irradiation of the light source and type of photodetector.

In some instances, the processor memory includes algorithm for determining a maximal differential signal amplitude. In one example, the processor memory includes algorithm for detecting a plurality of sets of first and second light signals; calculating a differential signal amplitude for each set of first and second light signals and determining the maximal differential signal amplitude from the plurality of calculated differential signal amplitudes. The subject systems may also be configured to determine the position of irradiation by the light source on the flow stream that produces the maximal differential signal amplitude between the first light signal and the second lights signal. For example, systems of interest may include one or more image capturing sensors for mapping the spatial position of the irradiation on the flow stream in an X-Y plane.

In certain embodiments, systems are configured to adjust the position of the light source in response to the assessed alignment between the light source and the flow stream. For example, the processor memory may include instructions for adjusting the light source where the calculated differential signal amplitude between the first signal and the second signal that is determined to be less than maximal to a position in an X-Y plane which produces a maximal differential signal amplitude between a first light signal and second light signal. The processor may, in some instances, include algorithm for mapping the position of the light source in the X-Y plane that produces the maximal differential signal amplitude between a first light signal and second light signal and matching the position of the light source in the X-Y plane with the position which produces the maximal differential signal amplitude between a first light signal and second light signal. To adjust the light source to a position which produces a maximal differential signal amplitude between a first light signal and second light signal, the subject systems may be configured to move the light source, such as on a support stage, or by changing the position, configuration or orientation of one or more optical adjustment protocols (e.g., changing the tilt of a lens or mirror).

In certain embodiments, the subject systems are configured to automatically align the light source with flow stream. In these embodiments, systems include a processor having memory with instructions for determining a position of irradiation on the flow stream that produces the maximal differential signal amplitude between the first signal and the second signal, instructions for determining a current position of light irradiation on the flow stream in an X-Y plane and instructions for adjusting the position of light irradiation to match the position of irradiation on the flow stream that produces the maximal differential signal amplitude between the first signal and the second signal.

Figure 2:
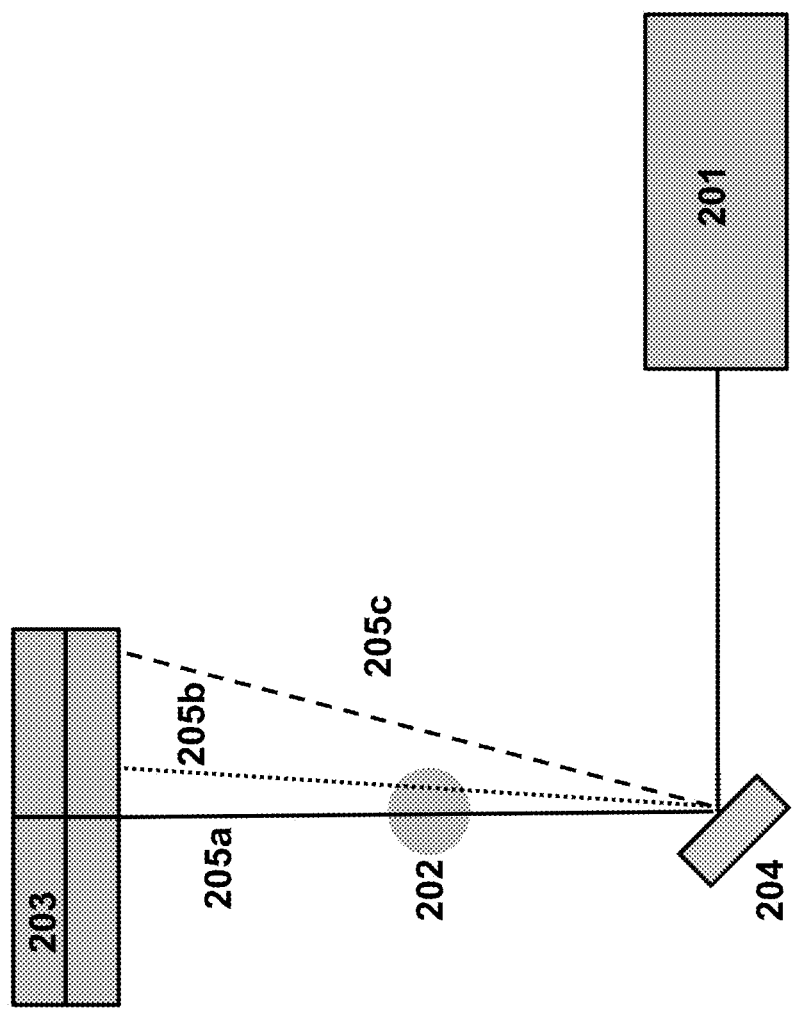
FIG. 2 illustrates a top-view illustration of a system suitable for practicing the subject methods according to certain embodiments.

FIG. 2 illustrates a top-view illustration of a system suitable for practicing the subject methods according to certain embodiments. Light source 201 irradiates flow stream 202 through optical adjustment protocol (mirror) 204 and forward propagated (e.g., scattered) light signals are detected by photodetector (e.g., quadrant photodiode) 203. As described herein, the differential signal amplitude depends on the position of irradiation by light source 201 on flow stream 202. Irradiation at the center (205a) of the flow stream along the horizontal axis provides a maximal differential signal amplitude as compared to the differential signal amplitude where irradiation by light source 201 is at an edge of the flow stream (205b). No light signal is detected where the position of irradiation by the light source falls outside of the flow stream (205c).

Aspects of the invention further include flow cytometric systems configured to carry out the above described methods. Suitable flow cytometry systems and methods for analyzing samples include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem.* January; 49(pt 1):17-28; Linden, et. al., *Semin Throm Hemost.* 2004 October; 30(5):502-11; Alison, et al. *J Pathol,* 2010 December; 222(4):335-344; and Herbig, et al. (2007) *Crit Rev Ther Drug Carrier Syst.* 24(3): 203-255; the disclosures of which are incorporated herein by reference. In certain instances, flow cytometry systems of interest include BD Biosciences FACSCanto™ flow cytometer, BD Biosciences FACSVantage™, BD Biosciences FACSort™, BD Biosciences FACSCount™, BD Biosciences FACScan™, and BD Biosciences FACSCalibur™ systems, a BD Biosciences Influx™ cell sorter, BD Biosciences Jazz™ cell sorter and BD Biosciences Aria™ cell sorter or the like.

In certain embodiments, the subject systems are flow cytometer systems which incorporate one or more components of the flow cytometers described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494 and 9,097,640; the disclosures of which are herein incorporated by reference.

In certain embodiments, flow cytometers of interest are configured to include a flow cell nozzle which is configured to propagate light emitted by a sample in a flow stream upstream through the nozzle orifice by total internal reflectance. The term "propagate" is used herein in its conventional sense to refer to the travel of light through the fluid medium of the flow stream where the path of propagated light is a function of the refraction, reflection, diffraction and interference by the fluid medium. In these embodiments, the flow cytometer includes a flow cell nozzle that propagates and collects light in a direction which is opposite to the direction of fluid flow by the flow stream. In other words, where the flow stream has fluidic flow along the positive Y direction along the Y axis in an X-Y plane, light signals from light propagated upstream by total internal reflectance traverses in the negative Y direction. The phrase "total internal reflectance" is used herein in its conventional sense to refer to the propagation of electromagnetic waves within the boundaries of a fluid medium (e.g., flow stream) such that when a propagating wave strikes the medium boundary at an angle larger than the critical angle with respect to the normal to the surface, the electromagnetic wave is internally reflected.

Flow cell nozzles according to these embodiments includes a nozzle chamber having a proximal end where light propagated upstream is collected and a distal end having a nozzle orifice in fluid communication with the flow stream. In some instances, the flow cell nozzle includes a proximal cylindrical portion defining a longitudinal axis and a distal frustoconical portion which terminates in a flat surface having the nozzle orifice that is transverse to the longitudinal axis. The angle of the frustoconical walls of the flow nozzle relative to the longitudinal axis of the flow stream may vary, in certain embodiments, ranging from 120° to 160°. In certain embodiments, the walls of the nozzle chamber are reflective. The proximal end of the flow cell nozzle in flow cytometers of interest may include a sample injection port to provide sample (e.g., a biological sample) to the flow cell and a sheath fluid injection port which provides sheath fluid to the flow cell nozzle.

In some instances, the flow cell nozzle includes one or more optical adjustment components. By "optical adjustment" is meant that emitted light propagated upstream from the flow stream through the nozzle orifice is changed as desired before being conveyed to a detector (as discussed in greater detail below) for measurement. For example, the optical adjustment may be to increase the dimensions of the collected beam of light, to focus the collected beam of light onto the surface of a detector or to collimate the beam of light. In some instances, optical adjustment is a magnification protocol so as to increase the beam spot produced by the light beam propagated through the nozzle orifice by total internal reflectance within the flow stream. In other instances, optical adjustment is a focusing protocol to reduce the dimensions of the beam spot.

In some embodiments, flow cell nozzles and flow cytometer systems of interest that are configured to propagate light emitted by a sample upstream through the flow stream by total internal reflectance include those described in U.S. Patent Publication No. US 2014-032861 published on Oct. 30, 2014, the disclosure of which is herein incorporated by reference. In some embodiments, systems of interest are systems that are configured to align a light collection system of the flow cytometer in accordance with the methods and devices described in U.S. Patent Publication No. US 2016-0170168 published on Jun. 16, 2016, the disclosure of which is herein incorporated by reference.

Computer-Controlled Systems

Aspects of the present disclosure further include computer controlled systems for practicing the subject methods, where the systems further include one or more computers for complete automation or partial automation of a system for practicing methods described herein. In some embodiments, systems include a computer having a computer readable storage medium with a computer program stored thereon, where the computer program when loaded on the computer includes instructions for detecting first and second light signals at different times along a vertical axis of a laser irradiated flow stream; algorithm for determining the spatial position of the flow stream in the detection field; algorithm for calculating a differential signal amplitude between the first signal and second signal; and instructions for assessing alignment of the light source (e.g., laser) with the flow stream based on the calculated differential signal amplitude between the first light signal and second light signal. In certain instances, systems include a computer having a computer readable storage medium with a computer program stored thereon, where the computer program when loaded on the computer further includes instructions having one or more of: algorithm for determining a maximal differential signal amplitude between the first signal and the second signal; algorithm for adjusting the irradiation on the flow stream by the light source to the position in the X-Y plane that produces the maximal differential signal amplitude between the first light signal and second light signal and algorithm for determining a position of irradiation on the flow stream by the light source in an X-Y plane that produces the maximal differential signal amplitude between the first signal and the second signal. In certain embodiments, the computer program when loaded on the computer further includes instructions having algorithm for determining a position of irradiation on the flow stream that produces the maximal differential signal amplitude between the first signal and the second signal; algorithm for determining a current position of light irradiation on the flow stream in an X-Y plane; and algorithm for adjusting the position of light irradiation to match the position of irradiation on the flow stream that produces the maximal differential signal amplitude between the first signal and the second signal.

In embodiments, the system includes an input module, a processing module and an output module. Processing modules of interest may include one or more processors that are configured and automated to assess alignment of a light source and flow stream and adjust the position of the light source in response to the assessed alignment as described above. For example processing modules may include two or more processors that are configured and automated to assess alignment of a light source and flow stream and adjust the position of the light source in response to the assessed alignment, such as three or more processors, such as four or more processors and including five or more processors. In some embodiments, the subject systems may include an input module such that parameters or information about the light source, flow stream, photodetectors, etc. may be input before practicing the subject methods.

As described above, each processor includes memory having a plurality of instructions for performing one or more steps of the subject methods (as described above), such as detecting first and second light signals at different times along a vertical axis of an irradiated flow stream; calculating a differential signal amplitude between the first light signal and second light signal to assess the alignment of the laser with the flow stream; determining a maximal differential signal amplitude between the first light signal and second light signal; comparing the calculated differential signal amplitude with the maximal signal amplitude and adjusting the position of the light source to a position which produces a maximal signal amplitude.

The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

Systems may include a display and operator input device. Operator input devices may, for example, be a keyboard, mouse, or the like. The processing module includes a processor which has access to a memory having instructions stored thereon for performing the steps of the subject methods. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques. The processor may be any suitable analog or digital system. In some embodiments, processors include analog electronics which allows the user to manually align a light source with the flow stream based on the first and second light signals. In some embodiments, the processor includes analog electronics which provide feedback control, such as for example negative feedback control.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid state storage devices (including magnetic or optical disks or tape or RAM, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; portable flash drive; and hybrids of these categories such as magnetic/optical storage media.

The processor may also have access to a communication channel to communicate with a user at a remote location. By remote location is meant the user is not directly in contact with the system and relays input information to an input manager from an external device, such as a computer connected to a Wide Area Network ("WAN"), telephone network, satellite network, or any other suitable communication channel, including a mobile telephone (i.e., smartphone).

In some embodiments, systems according to the present disclosure may be configured to include a communication interface. In some embodiments, the communication interface includes a receiver and/or transmitter for communicating with a network and/or another device. The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

In one embodiment, the communication interface is configured to include one or more communication ports, e.g., physical ports or interfaces such as a USB port, an RS-232 port, or any other suitable electrical connection port to allow data communication between the subject systems and other external devices such as a computer terminal (for example, at a physician's office or in hospital environment) that is configured for similar complementary data communication.

In one embodiment, the communication interface is configured for infrared communication, Bluetooth® communication, or any other suitable wireless communication protocol to enable the subject systems to communicate with other devices such as computer terminals and/or networks, communication enabled mobile telephones, personal digital assistants, or any other communication devices which the user may use in conjunction.

In one embodiment, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or WiFi connection to the internet at a WiFi hotspot.

In one embodiment, the subject systems are configured to wirelessly communicate with a server device via the communication interface, e.g., using a common standard such as 802.11 or Bluetooth® RF protocol, or an IrDA infrared protocol. The server device may be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touch-screen.

In some embodiments, the communication interface is configured to automatically or semi-automatically communicate data stored in the subject systems, e.g., in an optional data storage unit, with a network or server device using one or more of the communication protocols and/or mechanisms described above.

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g., over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Windows XP, Windows 7, Windows 8, iOS, Sun Solaris, Linux, OS/400, Compaq Tru64 Unix, SGI IRIX, Siemens Reliant Unix, and others.

Utility

The subject systems, methods, and computer systems find use in a variety of different applications where it is desirable to automate alignment of a light source with a flow stream, such as aligning a laser with a flow stream in a flow cytometer. Embodiments of the present disclosure find use where minimizing the amount of reliance on human input and adjustments to the system are desired, such as in research and high throughput laboratory testing. The present disclosure also finds use in flow cytometry where it is desirable to provide a flow cytometer with improved cell sorting accuracy, enhanced particle collection, reduced energy consumption, particle charging efficiency, more accurate particle charging and enhanced particle deflection during cell sorting. In embodiments, the present disclosure reduces the need for user input or manual adjustment during sample analysis with a flow cytometer. In certain embodiments, the subject systems provide fully automated protocols so that adjustments to a flow cytometer during use require little, if any human input.

The present disclosure also finds use in applications where cells prepared from a biological sample may be desired for research, laboratory testing or for use in therapy. In some embodiments, the subject methods and devices may facilitate the obtaining individual cells prepared from a target fluidic or tissue biological sample. For example, the subject methods and systems facilitate obtaining cells from fluidic or tissue samples to be used as a research or diagnostic specimen for diseases such as cancer. Likewise, the subject methods and systems facilitate obtaining cells from fluidic or tissue samples to be used in therapy. Methods and devices of the present disclosure allow for separating and collecting cells from a biological sample (e.g., organ, tissue, tissue fragment, fluid) with enhanced efficiency and low cost as compared to traditional flow cytometry systems.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of assessing alignment of a laser with a flow stream, the method comprising:
    irradiating with the laser a particle in the flow stream at a first position on the particle to produce a first light signal and at a second position on the particle to produce a second light signal;
    detecting the first and second light signals at different times; and
    calculating a differential signal amplitude between the first signal and second signal to assess the alignment of the laser with the flow stream.

2. The method according to claim 1, wherein the method comprises detecting first and second light signals from laser irradiated perturbations in the flow stream.

3. The method according to claim 2, wherein the particle is a cell or bead.

4. The method according to claim 3, wherein the cell or bead produces the perturbations in the flow stream.

5. The method according to claim 1, wherein the first and second light signals comprise scattered light detected by a detector adjacent to the flow stream in a forward configuration from laser irradiation.

6. The method according to claim 1, wherein the first light signal comprises light that is refracted upward from the flow stream.

7. The method according to claim 1, wherein the second signal comprises light that is refracted downward from the flow stream.

8. The method according to claim 1, further comprising determining a maximal differential signal amplitude between the first signal and the second signal.

9. The method according to claim 8, further comprising determining a position of laser irradiation on the flow stream along a horizontal axis orthogonal to the longitudinal axis of the flow stream that produces the maximal differential signal amplitude between the first signal and the second signal.

10. The method according to claim 9, further comprising adjusting the laser irradiation on the flow stream to the position along the horizontal axis that produces the maximal differential signal amplitude between the first signal and second signal.

11. The method according to claim 10, further comprising determining with a detector the adjusted position of laser irradiation along the horizontal axis.

12. The method according to claim 11, further comprising maintaining laser irradiation on the flow stream at the adjusted position along the horizontal axis that produces the maximal differential signal amplitude between the first signal and second signal for an extended period of time.

13. The method according to claim 8, further comprising determining a position of laser irradiation on the flow stream in an X-Y plane that produces the maximal differential signal amplitude between the first signal and the second signal.

14. The method according to claim 13, further comprising adjusting the laser irradiation on the flow stream to the position in the X-Y plane that produces the maximal differential signal amplitude between the first signal and second signal.

15. The method according to claim 13, further comprising maintaining laser irradiation on the flow stream at the position in the X-Y plane that produces the maximal differential signal amplitude between the first signal and second signal for an extended period of time.

16. The method according to claim 1, wherein the first and second light signals are detected along a vertical axis of the flow stream at periodic intervals.

17. The method according to claim 1, wherein the first and second light signals are continuously detected along a vertical axis of the flow stream.

18. The method according to claim 1, wherein the first and second light signals are detected with a position sensing detector.

19. A system for assessing alignment of a laser with a flow stream, the system comprising:
- a laser configured to irradiate a particle in the flow stream at a first position on the particle to produce a first light signal and at a second position on the particle to produce a second light signal;
- a sensor configured to detect the first light signal and the second light signal at different times; and
- a processor comprising memory operably coupled to the processor, wherein the memory includes instructions stored thereon to calculate a differential signal amplitude between the first and second signals to assess the alignment of the laser with the flow stream.

20. A system for assessing alignment of a laser with a flow stream comprising a processor comprising memory operably coupled to the processor, wherein the memory includes instructions stored thereon, the instructions comprising:
- algorithm for irradiating with the laser a particle in the flow stream at a first position on the particle to produce a first light signal and at a second position on the particle to produce a second light signal;
- algorithm for detecting the first and second light signals at different times; and
- algorithm for calculating a differential signal amplitude between the first signal and second signal; and
- algorithm for assessing alignment of the laser with the flow stream based on the calculated differential signal amplitude between the first signal and second signal.

21. The method according to claim 1, wherein the first signal is produced by irradiating the top of the particle and the second light signal is produced by irradiating the bottom of the particle.

22. The method according to claim 21, wherein the method comprises detecting two or more light signals from irradiating the first position on the particle and detecting two more light signals from irradiating the second position on the particle.

23. The method according to claim 1, further comprising irradiating the particle at a third position on the particle to produce a third light signal.

* * * * *